(12) United States Patent
Shelly et al.

(10) Patent No.: US 9,302,068 B2
(45) Date of Patent: Apr. 5, 2016

(54) HUMIDITY CONTROL IN A PRESSURE SUPPORT SYSTEM

(75) Inventors: Benjamin Irwin Shelly, Pittsburgh, PA (US); Bryan Richard McFadden, Derry, PA (US); Mark William Dimatteo, Irwin, PA (US); Mark Barclay, Saxonburg, PA (US); Christopher Scott Lucci, Murrysville, PA (US); Michael Thomas Kane, Harrison City, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 720 days.

(21) Appl. No.: 13/513,023

(22) PCT Filed: Nov. 17, 2010

(86) PCT No.: PCT/IB2010/055223
§ 371 (c)(1),
(2), (4) Date: May 31, 2012

(87) PCT Pub. No.: WO2011/080601
PCT Pub. Date: Jul. 7, 2011

(65) Prior Publication Data
US 2012/0235312 A1     Sep. 20, 2012

Related U.S. Application Data

(60) Provisional application No. 61/290,349, filed on Dec. 28, 2009.

(51) Int. Cl.
*B01F 3/04*     (2006.01)
*A61M 16/16*   (2006.01)

(52) U.S. Cl.
CPC ............. *A61M 16/162* (2013.01); *A61M 16/16* (2013.01)

(58) Field of Classification Search
CPC ............................ A61M 16/16; A61M 16/162
USPC .............. 261/128, 142, 72.1, 119.1, DIG. 65; 128/203.17, 203.27, 204.14, 204.18
See application file for complete search history.

(56) References Cited

U.S. PATENT DOCUMENTS

| | | | | |
|---|---|---|---|---|
| 2,302,528 A | * | 11/1942 | Conklin | 236/44 A |
| 3,584,193 A | * | 6/1971 | Badertscher | 392/328 |
| 4,060,576 A | * | 11/1977 | Grant | 261/130 |

(Continued)

FOREIGN PATENT DOCUMENTS

| CN | 1809397 A | 7/2006 |
|---|---|---|
| CN | 101242867 A | 8/2008 |

(Continued)

*Primary Examiner* — Charles Bushey
*Assistant Examiner* — Scott Bushey
(74) *Attorney, Agent, or Firm* — Michael W. Haas

(57) ABSTRACT

A pressure support system configured to provide pressure support therapy includes a humidifier that holds an enhanced amount of liquid while enhancing the power consumption of the pressure support system and enabling relatively rapid adjustments to humidity level. The humidifier includes a humidification chamber and a holding chamber, and a partition that divides the holding chamber from the humidification chamber such that liquid from the holding chamber replenishes liquid held in the humidification chamber. The partition, however, also provides a level of thermal isolation for the humidification chamber from the holding chamber.

14 Claims, 4 Drawing Sheets

(56) References Cited

U.S. PATENT DOCUMENTS

| | | |
|---|---|---|
| 4,652,508 A | 3/1987 | Ober |
| 4,714,078 A | 12/1987 | Paluch |
| 4,993,411 A | 2/1991 | Callaway |
| 6,031,968 A * | 2/2000 | Holtmann ............ 392/402 |
| 6,169,852 B1 * | 1/2001 | Liao et al. ............ 392/395 |
| 6,997,183 B2 * | 2/2006 | Koch et al. ............ 128/203.17 |
| 7,386,225 B2 * | 6/2008 | Lin ............ 392/405 |
| 7,942,389 B2 * | 5/2011 | Koch et al. ............ 261/130 |
| 2003/0042629 A1 * | 3/2003 | Eom ............ 261/81 |
| 2004/0221843 A1 * | 11/2004 | Baecke ............ 128/203.16 |
| 2006/0191531 A1 | 8/2006 | Mayer |
| 2013/0239965 A1 * | 9/2013 | Shelly et al. ............ 128/203.26 |

FOREIGN PATENT DOCUMENTS

| | | |
|---|---|---|
| DE | 29617077 U1 | 2/1997 |
| WO | WO2004112873 A1 | 12/2004 |
| WO | WO2007019625 A1 | 2/2007 |

\* cited by examiner

HUMIDITY CONTROL IN A PRESSURE SUPPORT SYSTEM

CROSS-REFERENCE TO RELATED APPLICATIONS

This patent application claims the priority benefit under 35 U.S.C. §371 of international patent application no. PCT/IB2010/055223, filed Nov. 17, 2010, which claims the priority benefit under 35 U.S.C. §119(e) of U.S. Provisional Application No. 61/290,349 filed on Dec. 28, 2009, the contents of which are herein incorporated by reference.

BACKGROUND OF THE INVENTION

1. Field of the Disclosure

The invention relates to a pressure support system configured to provide pressure support therapy to a subject, wherein the pressure support system comprises a humidifier configured to control the humidity of gas provided to the subject by the pressure support system.

2. Description of the Related Art

Pressure support systems that provide pressure support therapy to the airway of a subject are known. Some conventional pressure support systems include humidifiers configured to control the level of humidity of gas provided to the subject during pressure support therapy. In conventional pressure support systems, increasing a capacity to hold liquid for use in the humidifier may enhance the convenience of the pressure support system to users. However, typically, increasing the capacity to hold liquid in a pressure support system humidifier may increase the power budget of the device, increase the amount of time required to initialize the pressure support system, and/or increase the time it takes the pressure support system to adjust the humidity of the gas from one level to another during therapy.

SUMMARY OF THE INVENTION

Accordingly, it is an object of the present invention to provide a pressure support system that overcomes the shortcomings of conventional pressure support systems. This object is achieved according to one embodiment of the present invention by providing a pressure support system configured to generate a flow of gas for delivery to an airway of a subject that includes a humidifier configured to humidify the flow of gas. In one embodiment, the humidifier comprises a holding chamber, a humidification chamber, a heating element, and a partition. The humidification chamber is positioned adjacent to the holding chamber, and defines a flow path between a gas inlet and a gas outlet. The gas inlet is configured to receive a flow of gas into the humidification chamber and the gas outlet configured to release the flow of gas from the humidification chamber. The heating element is configured to controllably elevate the temperature of fluid within the humidification chamber to heat liquid within humidification chamber such that the gas flowing through the humidification chamber from the gas inlet to the gas outlet is humidified by the heated liquid. The partition is configured to divide the humidification chamber from the holding chamber, wherein the partition defines an opening between the humidification chamber and the holding chamber such that fluid is communicated between the humidification chamber and the holding chamber through the opening. The opening is formed such that the partition and liquid held in the humidification chamber isolate the flow path formed by humidification chamber from the holding chamber causing the flow of gas through the humidification chamber to result in pressurization of the humidification chamber that reduces the level of liquid within the humidification chamber to a level that is substantially lower than the level of liquid in the holding chamber.

Another aspect of the invention relates to a method of humidifying a flow of gas generated by a pressure support system for delivery to an airway of a subject. In one embodiment the method comprises holding liquid in a humidification chamber that forms a flow path between a gas inlet and a gas outlet, the gas inlet being configured to receive gas into the humidification chamber and the gas outlet being configured to release gas from the humidification chamber; directing a flow of gas through the humidification chamber along the flow path from the gas inlet to the gas outlet such that the humidification chamber is pressurized by the flow of gas; controllably elevating the temperature of fluid within the humidification chamber to heat the liquid within humidification chamber such that the flow of gas flowing through the humidification chamber from the gas inlet to the gas outlet is humidified by the heated liquid; and receiving liquid from the humidification chamber into a holding chamber positioned adjacent to the humidification chamber as the flow of gas elevates pressure within the humidification chamber, wherein the holding chamber is divided from the humidification chamber by a partition that defines an opening between the humidification chamber and the holding chamber through which the liquid is received, wherein the opening and holding chamber are formed such that the reception of liquid from the humidification chamber into the holding chamber causes the level of liquid within the humidification chamber to be reduced to a level that is substantially lower than the level of liquid in the holding chamber.

Yet another aspect of the invention relates to a pressure support system configured to generate a flow of gas for delivery to an airway of a subject, the pressure support system comprising a system configured to humidify the flow of gas. In one embodiment, the system comprises means for forming a flow path between a gas inlet and a gas outlet, wherein the flow path is formed in fluid communication with a first reservoir of liquid held by the means for forming the flow path; means for introducing a flow of gas along the flow path that pressurizes the means for forming the flow path; means for controllably elevating the temperature of fluid within the means for forming the flow path to vaporize liquid within means for forming the flow path such that the flow of gas is humidified by the vaporized liquid; means for holding a second reservoir of liquid adjacent to the means for forming a flow path; and means for dividing the means for forming the flow path from the means for holding the second reservoir of liquid such that liquid in the first reservoir of liquid is in fluid communication with the second reservoir of liquid, wherein the means for dividing is formed such that pressurization of the means for forming the flow path by the flow of gas causes the level of the first reservoir of liquid to be reduced to a level that is substantially lower than the level of liquid in the second reservoir of liquid.

It is a further object of the present invention to provide a humidifier for use in a pressure support system. The humidifier includes a holding chamber and a humidification chamber positioned adjacent to the holding chamber. The humidification chamber defines a flow path between a gas inlet and a gas outlet. The gas inlet is configured to receive a flow of gas into the humidification chamber and the gas outlet configured to release the flow of gas from the humidification chamber. The humidifier further includes a partition configured to divide the humidification chamber from the holding chamber. The partition defines an opening between the humidification chamber and the holding chamber such that fluid is communicated between the humidification chamber and the holding chamber through the opening. The opening is formed such that the partition and liquid held in the humidification chamber isolate the flow path formed by humidification chamber from the holding chamber causing the flow of gas through the humidification chamber to result in pressurization of the humidification chamber that reduces the level of liquid within the humidification chamber to a level that is substantially lower than the level of liquid in the holding chamber.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn in proportion. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention.

BREIF DESCRIPTION OF THE DRAWINGS

FIG. 1 schematically illustrates a pressure support system configured to provide pressure support therapy to a subject, in accordance with one or more embodiments of the invention;

DETAILED DESCRIPTION OF EXEMPLARY EMBODIMENTS

Figure 1:
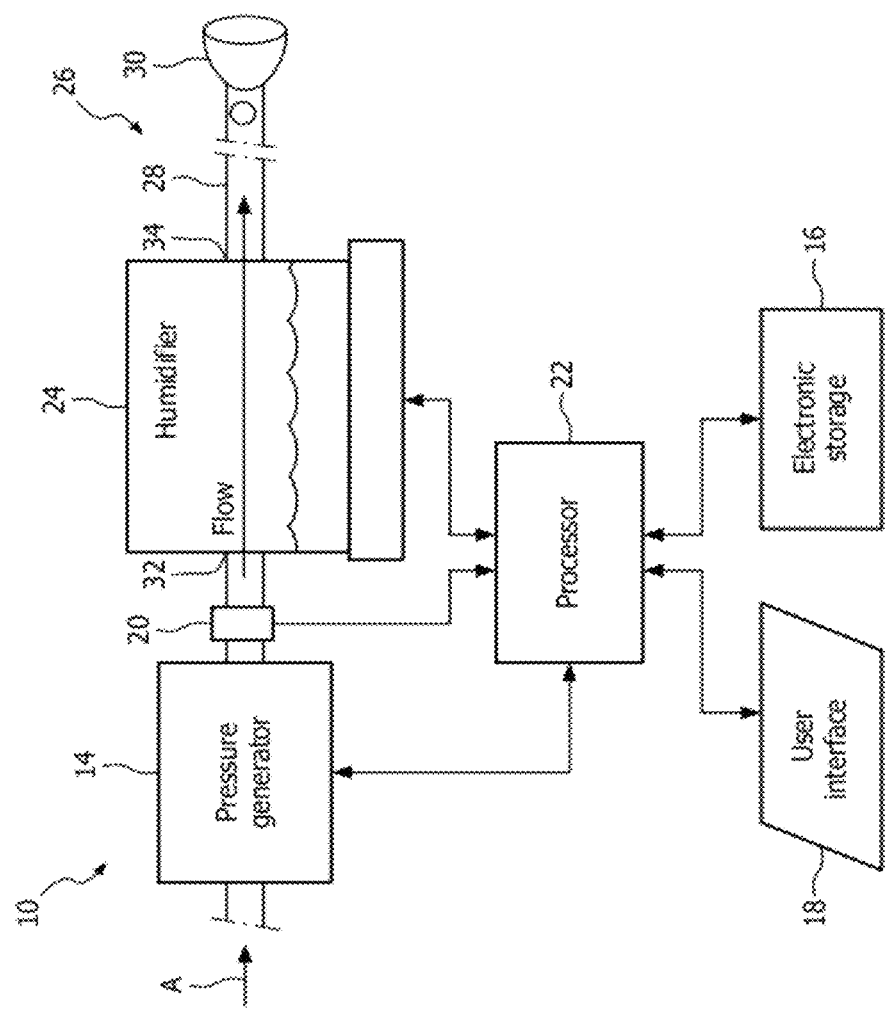

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a pressure support system 10 configured to provide pressure support therapy to a subject (not shown). Pressure support system 10 is configured to provide the pressure support therapy in the form of a flow of gas that is delivered to the airway of the subject. The pressure support therapy may be dynamic in that one or more parameters of the flow of gas generated by pressure support system 10 may be adjusted based on detection of one or more parameters. For example, pressure of the flow of gas may be increased based on changes to one or more parameters that indicate a respiratory event (e.g., an apnea, snoring, etc.). In one embodiment, pressure support system 10 includes one or more of a pressure generator 14, electronic storage 16, a user interface 18, a sensor 20, a processor 22, a humidifier 24, and/or other components.

In one embodiment, pressure generator 14 is configured to generate a flow of gas for delivery to the airway of the subject. The pressure generator 14 may control one or more parameters of the flow of gas (e.g., flow rate, pressure, volume, humidity, temperature, gas composition, etc.) for therapeutic purposes, or for other purposes. By way of non-limiting example, pressure generator 14 may be configured to control the flow rate and/or pressure of the flow of gas to provide pressure support to the airway of the subject.

Pressure generator 14 receives a flow of gas from a gas source, such as the ambient atmosphere, as indicated by arrow A and elevates the pressure of that gas for delivery to the airway of a patient. Pressure generator 14 is any device, such as a pump, blower, piston, or bellows, that is capable of elevating the pressure of the received gas for delivery to a patient. The present invention also contemplates that gas other than ambient atmospheric air may be introduced into circuit 12 for delivery to the patient. In such embodiments, a pressurized canister or tank of gas containing air, oxygen, or other breathable gas mixture can supply the intake of pressure generator 14.

In another embodiment, pressure generator 14 need not be provided, but instead the gas can by pressurized by the pressure of the canister or tank of pressurized gas itself, with the pressure delivered to the patient being controlled by a pressure regulator.

In one embodiment, pressure generator 14 is a blower that is driven at a substantially constant speed during the course of the pressure support treatment to provide the gas in gas delivery circuit 26 with a substantially constant elevated pressure and/or flow rate. The pressure generator 14 may include a valve for controlling the pressure/flow of gas. The present invention also contemplates controlling the operating speed of the blower, either alone or in combination with such a valve, to control the pressure/flow of gas provided to the patent. An example of a pressure support system suitable for use in the present invention is described in U.S. Pat. No. 6,105,575, hereby incorporated by reference in its entirety, and/or other pressure generation devices.

The flow of gas is delivered to the airway of the subject from pressure support system 10 via a gas delivery circuit 26. Gas delivery circuit 26 is configured to communicate the pressurized flow of gas generated by pressure generator 14 to the airway of the subject. As such, gas delivery circuit 26 includes a conduit 28 and a patient interface appliance 30. Conduit conveys the pressurized flow of gas to interface appliance 30, and interface appliance 30 delivers the flow of gas to the airway of the subject. Some examples of interface appliance 30 may include, for example, a nasal cannula, a nasal mask, a nasal/oral mask, a full face mask, a total face mask, and/or other interface appliances that communication a flow of gas with an airway of a subject. The present invention is not limited to these examples, and contemplates delivery of the flow of gas to the subject using any subject interface.

Although gas delivery circuit 26 is illustrated in FIG. 1 as a single-limbed circuit for the delivery of the flow of gas to the airway of the subject, this is not intended to be limiting. The scope of this disclosure includes double-limbed circuits having a first limb configured to both provide the flow of gas to the airway of the subject, and a second limb configured to selectively exhaust gas from gas delivery circuit 26 (e.g., to exhaust exhaled gases).

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media.

Electronic storage 16 may store software algorithms, information determined by processor 22, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., generator 14, user interface 18, processor 22, etc.).

User interface 18 is configured to provide an interface between system 10 and the subject through which the subject may provide information to and receive information from system 10. This enables data, cues, results, and/or instructions and any other communicable items, collectively referred to as "information," to be communicated between the subject and one or more of generator 14, electronic storage 16, and/or processor 22. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with generator 14.

It is to be understood that other communication techniques, either hard-wired or wireless, are also contemplated by the present invention as user interface 18. For example, the present invention contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present invention as user interface 18.

Sensor 20 is configured to generate output signals conveying information related to one or more parameters of the flow of gas and/or the breathing of the subject. The one or more parameters of the pressurized flow of breathable gas may include, for example, one or more of a flow rate, a volume, a pressure, humidity, temperature, acceleration, velocity, acoustics, changes in a parameter indicative of respiration, and/or other gas parameters. Sensor 20 may include one or more sensors that measure such parameters directly (e.g., through fluid communication with the flow of gas at pressure generator 14). Sensor 20 may include one or more sensors that generate output signals related to one or more parameters of the flow of gas indirectly.

For example, sensor 20 may include one or more sensors configured to generate an output based on an operating parameter of pressure generator 14 (e.g., a valve driver or motor current, voltage, rotational velocity, and/or other operating parameters), and/or other sensors. The one or more parameters of the breathing of the subject (that are not parameters of the flow of gas) may include other parameters that provide information about the breathing of the subject. For example, sensor 20 may include a transducer configured to detect acoustic waves transmitted to pressure support system 10 through gas delivery circuit 26. These acoustic waves may convey information related to respiratory effort of the subject, and/or the noise generated by the subject during respiration (e.g., during snoring).

Although sensor 20 is illustrated as a single sensor at a single location in pressure generator 14, this is not intended to be limiting. The sensor 20 may include a plurality of sensors which may be located proximately or separately with respect to each other. Sensors providing the functionality attributed herein to sensor 20 may be disposed in any of a plurality of locations, such as for example, within pressure generator 14, within (or in communication with) conduit 28, within (or in communication with) interface appliance 30, and/or other locations.

Processor 22 is configured to provide information processing capabilities in system 10. As such, processor 22 may include one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some implementations, processor 22 may include a plurality of processing units. These processing units may be physically located within the same device (e.g., pressure generator 14), or processor 22 may represent processing functionality of a plurality of devices operating in coordination.

Processor 22 is configured to control pressure generator 14 to generate the flow of gas in accordance with the therapy regime. By way of non-limiting example, processor 22 may control pressure generator 14 such that the pressure support provided to the subject via the flow of gas includes, non-invasive ventilation, positive airway pressure support, continuous positive airway pressure support, bi-level support, BiPAP®, and/or other types of pressure support therapy.

In controlling pressure generator 14, the therapy regime may dictate that the processor 22 be responsive to the output signals generated by sensor 20. For example, if the output signals generated by sensor 20 indicate that the subject is experiencing a respiratory event, the therapy regime may dictate that the processor 22 control pressure generator 14 to increase pressure of the flow of gas to help the subject overcome the event. Some non-limiting examples of respiratory events include an apnea (central or obstructive), a respiratory obstruction, snoring, hypopnea, flow limitation, and/or other respiratory events.

Humidifier 24 is configured to adjust the humidity of the flow of gas. In one embodiment humidifier 24 is a warm mist humidifier (e.g., a vaporizer) configured to generate water vapor by heating liquid held within humidifier 24. Humidifier 24 includes a gas inlet 32 and a gas outlet 34. The humidifier 24 is configured such that the flow of gas is received from pressure generator 14 by humidifier 24 through gas inlet 32 and is humidified within humidifier 24 by the water vapor before being released from humidifier 24 through gas outlet 34. In one embodiment, gas outlet 34 is connected with gas delivery circuit 26 such that the humidified flow of gas is delivered to the airway of the subject through gas delivery circuit 26.

Humidifier 24 is configured such that the amount by which the humidity of the flow of gas is adjusted within humidifier 24 is controlled by processor 22. For example, processor 22 may control a heating element (not shown in FIG. 1) configured to heat/vaporize liquid within humidifier 24 to adjust the amount of moisture added to the flow of gas within humidifier 24. The level of humidity to which the flow of gas is adjusted may be dictated by a therapy regime and/or selected by a user (e.g., the subject, a caregiver, a therapy decision-maker, etc.).

In conventional pressure support systems, the heating of liquid within a humidifier is a relatively large power sink. The amount of power required to maintain the heat of the liquid at a desired or selected level is dictated in part by the amount of water that is held by the humidifier. The amount of water held by the humidifier also impacts the amount of time it takes for the humidifier to begin humidification upon start-up of a conventional pressure support system, and the amount of time it takes for adjustments to humidification level to be executed. The larger the amount of water that is held by a humidifier in a conventional pressure support system, the more power that is consumed to heat the water to a desired or selected temperature. Further, the larger the amount of water, the longer it takes to bring the temperature of the water to a desired or selected level, and/or to adjust the water temperature. This creates a tension between design objectives in conventional pressure support systems.

For example, holding a relatively large amount of water in the humidifier may enhance the convenience and/or ease of use of the conventional pressure support system. However, holding a relatively large amount of water in the humidifier may substantially increase the power budget of the conventional pressure support system, increase an initialization time of the conventional pressure support system, and/or impair the adjustability of humidity level in the flow of gas generated by the conventional pressure support system. The humidifier 24 of pressure support system 10, on the other hand, is designed to enable humidifier 24 to hold a relatively large amount of water while reducing the drawbacks present in conventional pressure support systems.

Figure 2:
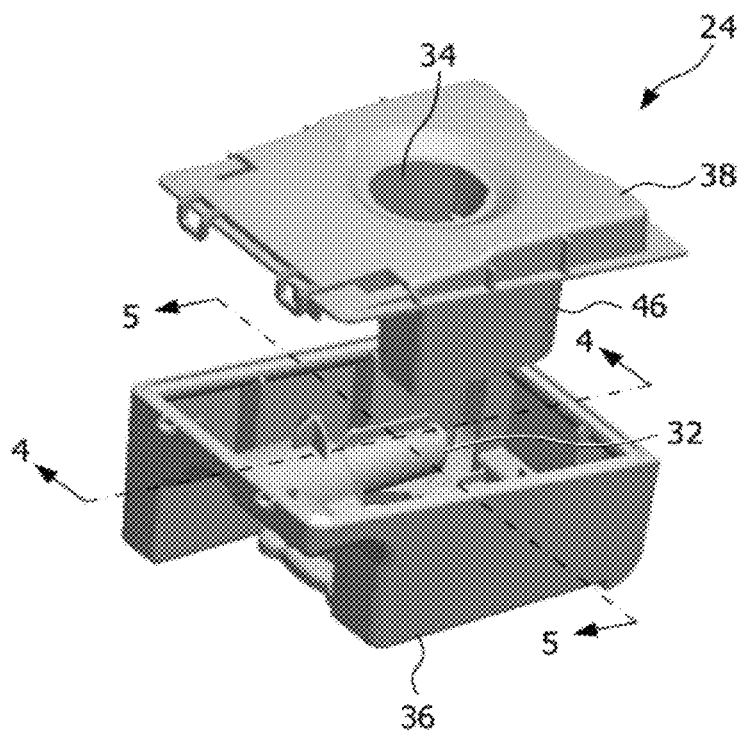
FIG. 2 illustrates a humidifier of a pressure support system according to one or more embodiments of the invention.
Figure 3:
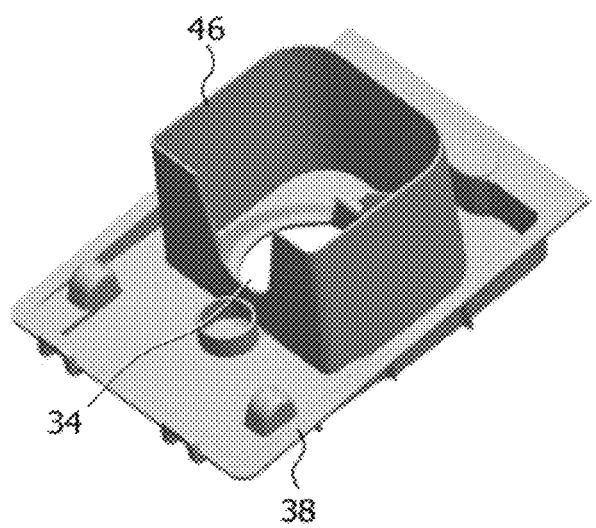
FIG. 3 illustrates a unitary partition structure of a humidifier of a pressure support system, according to one or more embodiments of the invention.

FIG. 2 illustrates an exploded view of one or more implementations of humidifier 24. In the view shown in FIG. 2, a unitary base structure 36 is exploded from a unitary partition structure 38. The orientation of unitary base structure 36 and unitary partition structure 38 shown is the orientation in which humidifier 24 would be deployed during use (e.g., with unitary base structure 36 positioned underneath unitary partition structure 38). Unitary base structure 36 and/or unitary partition structure 38 may be formed from polycarbonate, and/or other materials. Unitary base structure 36 forms gas inlet 32, and unitary partition structure 38 forms gas outlet 34. As is discussed below, a flow path is formed between gas inlet 32 and gas outlet 34 by unitary base structure 36 and unitary partition structure 38. FIG. 3 illustrates reverse elevation of one or more implementations of unitary partition structure 38. It will be appreciated that the description of humidifier 24 as being formed by unitary base structure 36 and unitary partition structure 38 is not intended to be limiting. The scope of this disclosure includes apparatuses having more or fewer pieces, and/or with pieces having different specific shapes.

Figure 4:
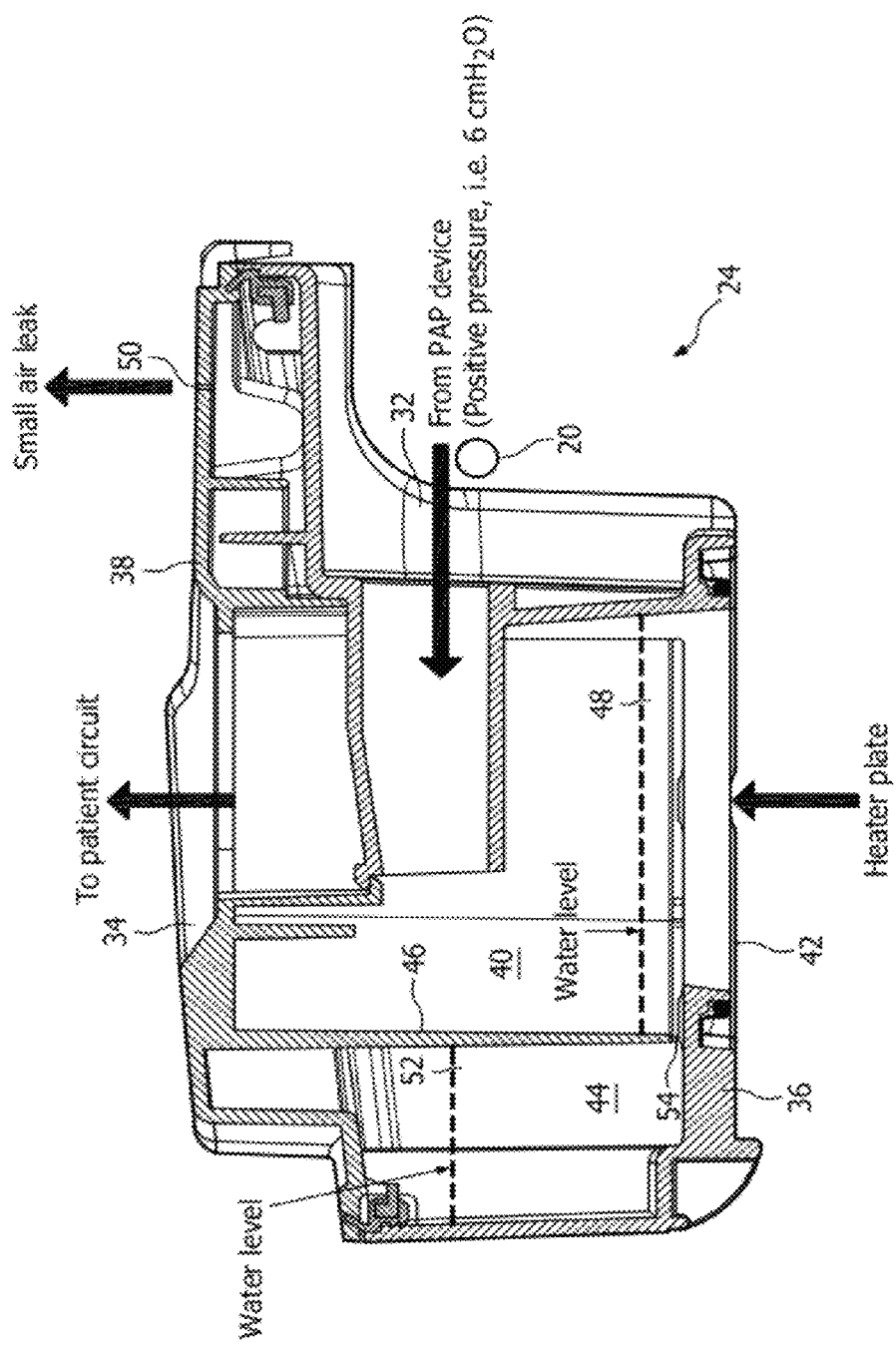
FIG. 4 illustrates a humidifier of a pressure support system according to one or more embodiments of the invention.
Figure 5:
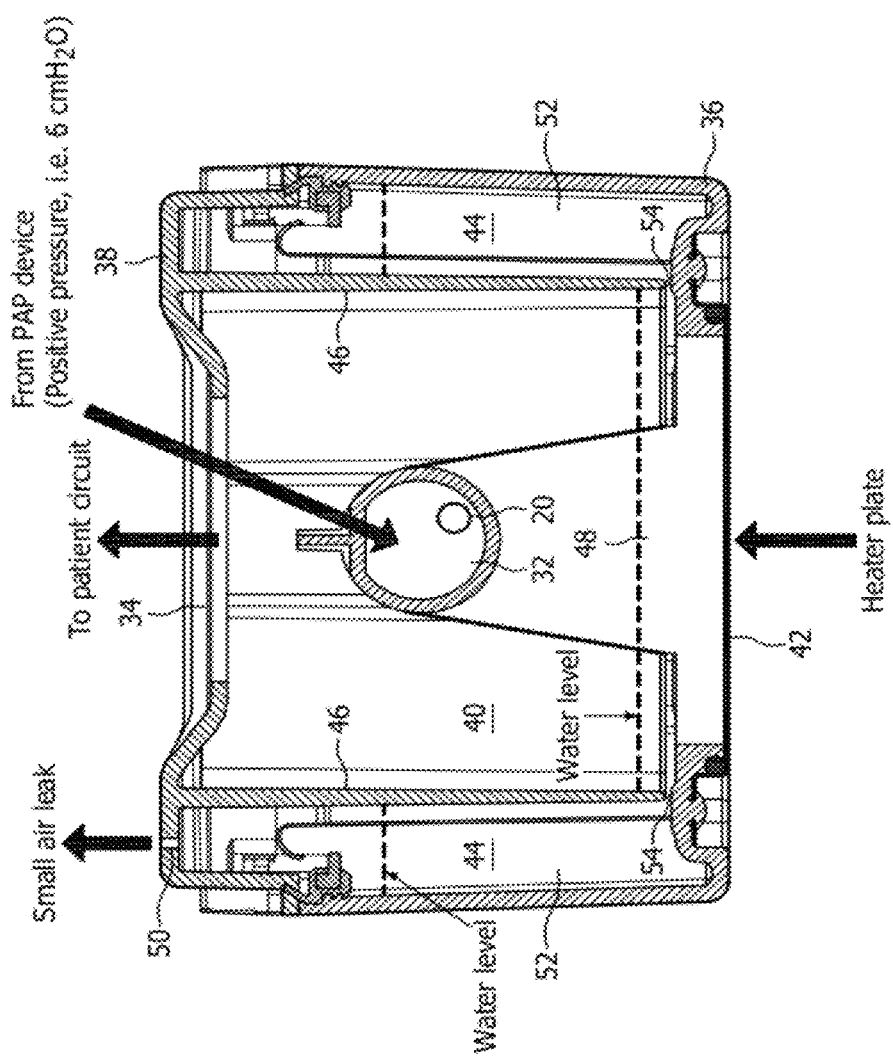
FIG. 5 illustrates a humidifier of a pressure support system, according to one or more embodiments of the invention.

FIGS. 4 and 5 illustrate sectional views of humidifier 24 with unitary base structure 36 and unitary partition structure 38 assembled. Specifically, FIG. 4 shows a sectional view taken along section line 4-4, and FIG. 5 shows a sectional view taken along section line 5-5. When assembled, humidifier 24 includes a humidification chamber 40, a heating element 42, a holding chamber 44, and a partition 46.

Humidification chamber 40 communicates with each of gas inlet 32 and gas outlet 34 to form a flow path through humidifier 24 that does not communicate with the holding chamber 44. As such, the flow of gas flowing through humidifier 24 flows through the flow path defined by humidification chamber 40 between gas inlet 32 and gas outlet 34. Humidification chamber 40 holds a first reservoir of liquid 48. During use, the first reservoir of liquid 48 is vaporized, and the vapor is picked up by the flow of gas within humidification chamber 40 while flowing along the flow path from gas inlet 32 to gas outlet 34. The humidification chamber 40 is sealed (or substantially sealed) from ambient atmosphere. The ceiling of humidification chamber 40 is formed by unitary partition structure 38, while the base of humidification chamber 40 is formed by unitary base structure 36.

Heating element 42 is configured to controllably elevate the temperature of fluid within humidification chamber 40. In the embodiment shown in FIGS. 4 and 5, heating element 42 is positioned at the bottom of humidification chamber 40 to be in proximity to first reservoir of liquid 48 such that heat emitted by heating element 42 is dispensed directly into first reservoir of liquid 48. This emission of heat by heating element 42 into first reservoir of liquid 48 vaporizes first reservoir of liquid 48. As was discussed above with respect to FIG. 1, the amount of heat emitted by heating element 42 is controllable by a processor (e.g., processor 22 shown in FIG. 1 and described above) to bring the humidity of the flow of gas to a selected level. As can be seen in FIGS. 4 and 5, in one embodiment, heating element 42 does not directly heat fluid within holding chamber 44.

Holding chamber 44 is positioned adjacent to humidification chamber 40. In one embodiment, holding chamber 44 at least partially surrounds humidification chamber 40. For example, in FIGS. 4 and 5, holding chamber 44 surrounds humidification chamber 40 on three sides. In one embodiment, a secondary opening 50 in humidifier 24 forms a restrictive flow path between chamber 44 ambient atmosphere. In one embodiment, chamber 44 does not include secondary opening 50. Holding chamber 44 is configured to hold a second reservoir of liquid 52. The base and at least one of the side walls of holding chamber 44 are formed by unitary base structure 36.

Partition 46 is configured to divide humidification chamber 40 from holding chamber 44. In dividing humidification chamber 40 from holding chamber 44, partition 46 defines an opening 54 between humidification chamber 40 and holding chamber 44. The opening 54 is located such that first reservoir of liquid 48 is placed in fluid communication with second reservoir of liquid 52.

For example, in the implementations shown in FIGS. 4 and 5, opening 54 is formed toward the bottom of humidification chamber 40 and holding chamber 44. More specifically, partition 46 is formed to extend not all the way to the base of humidification chamber 40 and holding chamber 44 such that opening 54 is formed underneath partition 46. The gap between the bottom of partition 46 and unitary base structure 36 forming opening 54 may be about 1.5 mm. In one embodiment, the partition 46 and opening 54 are formed such that fluid communication between first reservoir of liquid 48 and second reservoir of liquid 52 is unrestricted by any valve or nozzle, but instead enables liquid to pass back and forth between first reservoir of liquid 48 and second reservoir of liquid 52.

The size and/or shape of opening 54 enables heating element 42 to heat first reservoir of liquid 48 to a desired or selected temperature without a substantial amount of the heat emitted by heating element 42 being absorbed by liquid within second reservoir of liquid 52. This enables humidifier 24 to hold the liquid in second reservoir of liquid 52 without having to heat second reservoir of liquid 52 along with first reservoir of liquid 48, or to adjust the humidity level of the flow of gas. Instead, since second reservoir of liquid 52 is kept in relative (though not complete) thermal isolation from first reservoir of liquid 48 by partition, power is conserved, and changes to the temperature of first reservoir of liquid 48 can be effected without having to make the same adjustments to the temperature of the liquid within second reservoir of liquid 52. However, because of opening 54, liquid from second reservoir of liquid 52 can pass into first reservoir of liquid 48 to replenish first reservoir of liquid 48 as liquid within humidification chamber 40 is vaporized and carried out of humidifier 24 by the flow of gas. Therefore, the configuration of humidification chamber 40, heating element 42, holding chamber 44, partition 46, and opening 54, provides the benefits of an enhanced amount of liquid storage while mitigating at least some of the drawbacks associated with storing a relatively large amount of liquid in a humidifier of a pressure support system.

During operation, the pressure within humidification chamber 40 is increased by the pressure of the flow of gas as it flows through humidification chamber 40. This increase in pressure is substantial, and may increase the pressure in humidification chamber to at least about 4 cmH$_2$O. The opening 54 is formed such that in response to this increase in pressure elevation in humidification chamber 40 liquid in the first reservoir of liquid 48 can flow from humidification chamber 40 through opening 54 and into holding chamber 44 to join second reservoir of liquid 52. Because opening 54 does not enable gas within holding chamber 44 to communicate directly with gas in humidification chamber 40, flow of liquid from the first reservoir of liquid 48 to the second reservoir of liquid 52 causes the level of the liquid in second reservoir of liquid to rise and the level of the liquid in the first reservoir of liquid to drop.

For example, FIGS. 4 and 5 illustrate the manner in which the liquid levels in humidification chamber 40 and holding chamber 44 may be adjusted by the pressurization of humidification chamber 40 as the flow of gas flows through the flow path defined by humidification chamber 40. The liquid level in humidification chamber 40 during operation will become substantially lower than the liquid level in holding chamber 40. By way of example, the level of the first reservoir of liquid 48 may be at least about 24 mm lower than the level of the second reservoir of liquid 52. As another example, the level of the first reservoir of liquid 48 may at least be about 15 mm lower than the level of the second reservoir of liquid 52. As another example, the level of the first reservoir of liquid 48 may be at least about 30 mm lower than the level of the second reservoir of liquid 52.

This shift in liquid from humidification chamber 40 to holding chamber 44 may further enhance the manner in which the design of humidifier 24 avoids at least some of the drawbacks associated with increased liquid storage capacity. For example, as the amount of liquid within humidification chamber 40 is reduced, the heat from heating element 42 required to adjust and/or maintain a water temperature within first reservoir of liquid 48 is reduced. As another example, the reduction of liquid within first reservoir of liquid 48 caused by the increased temperature in humidification chamber 40 also enables humidifier 24 to respond with an enhanced speed to control commands received (e.g., from a processor) to adjust the humidity level of the flow of gas (e.g., by increasing or reducing the temperature of first reservoir of liquid 48).

It will be appreciated, however, that the changes in the levels of first reservoir of liquid 48 and second reservoir of liquid 52 caused by the flow of the flow of gas through the flow path defined by humidification chamber 40 does not impede replenishment of first reservoir of liquid 48 from second reservoir of liquid 52. As liquid from first reservoir of liquid 48 is vaporized and carried out of humidification chamber 40 by the flow of gas, liquid from second reservoir of liquid 52 passes through opening 54 to replenish first reservoir of liquid 48.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of humidifying a flow of gas generated by a pressure support system for delivery to an airway of a subject, the pressure support system, the method comprising:

holding liquid in a humidification chamber that forms a flow path between a gas inlet and a gas outlet, the gas inlet being configured to receive a flow gas into the humidification chamber and the gas outlet being configured to release the flow of gas from the humidification chamber;

directing such a flow of gas through the humidification chamber along the flow path between the gas inlet and the gas outlet such that the humidification chamber is pressurized by the flow of gas;

controllably heating the liquid within the humidification chamber separately from the liquid held in a holding chamber such that the flow of gas flowing through the humidification chamber from the gas inlet to the gas outlet is humidified by the heated liquid; and receiving liquid from the humidification chamber into the holding chamber positioned adjacent to the humidification chamber as the flow of gas elevates pressure within the humidification chamber, wherein the holding chamber is divided from the humidification chamber by a partition that defines an opening between the humidification chamber and the holding chamber through which the liquid is received, and wherein the opening and holding chamber are formed such that the reception of liquid from the humidification chamber into the holding chamber causes the level of liquid within the humidification chamber to be reduced to a level that is substantially lower than the level of liquid in the holding chamber.

2. The method of claim 1, wherein the holding chamber at least partially surrounds the humidification chamber.

3. The method of claim 1, wherein the humidification chamber is sealed from ambient atmosphere, and wherein the holding chamber forms an secondary opening that places the holding chamber in restrictive communication with ambient atmosphere.

4. The method of claim 1, further comprising replenishing the liquid within the humidification chamber from the holding chamber as the liquid within the humidification chamber is vaporized and carried out of the humidification chamber by the flow of gas.

5. The method of claim 1, wherein a base surface of the humidification chamber and the holding chamber, and at least one side wall of the humidification chamber are formed by a unitary base structure, and wherein the partition and a ceiling of the humidification chamber are formed by a unitary partition structure.

6. The method of claim 5, further comprising forming the gas inlet with the unitary base structure and the gas outlet with the unitary partition structure.

7. A pressure support system comprising:
(a) a pressure generator adapted to generate a flow of gas and
(b) a humidifier configured to humidify the flow of gas, the humidifier comprising;
(1) a holding chamber;
(2) a humidification chamber positioned adjacent to the holding chamber, the humidification chamber defining a flow path between a gas inlet and a gas outlet, the gas inlet being configured to receive the flow of gas into the humidification chamber and the gas outlet configured to release the flow of gas from the humidification chamber;
(3) a heating element configured to controllably heat liquid within the humidification chamber separately from the liquid held in the holding chamber such that the flow of gas through the humidification chamber from the gas inlet to the gas outlet is humidified by the heated liquid;
(4) a partition configured to divide the humidification chamber from the holding chamber, wherein the partition defines an opening between the humidification chamber and the holding chamber such that fluid is communicated between the humidification chamber and the holding chamber through the opening, and wherein the opening is formed such that the partition and liquid held in the humidification chamber isolate the flow path formed by humidification chamber from the holding chamber causing the flow of gas through the humidification chamber to result in pressurization of the humidification chamber that reduces the level of liquid within the humidification chamber to a level that is substantially lower than the level of liquid in the holding chamber;
(5) a unitary base structure configured to form a base surface of the humidification chamber and the holding chamber, and at least one side wall of the humidification chamber; and
(6) a unitary partition structure configured to form the partition and a ceiling of the humidification chamber, wherein the unitary base structure forms the gas inlet and the unitary partition structure forms the gas outlet.

8. The pressure support system of claim 7, wherein the holding chamber at least partially surrounds the humidification chamber.

9. The pressure support system of claim 7, wherein the humidification chamber is sealed from ambient atmosphere, and wherein the holding chamber forms a secondary opening that places the holding chamber in restrictive communication with ambient atmosphere.

10. The pressure support system of claim 7, wherein the opening formed by the partition is configured such that liquid from the holding chamber replenishes the liquid within the humidification chamber as the liquid within the humidification chamber is vaporized and carried out of the humidifier by the flow of gas.

11. A humidifier for use in a pressure support system, the humidifier comprising:
a holding chamber;
a humidification chamber positioned adjacent to the holding chamber, the humidification chamber defining a flow path between a gas inlet and a gas outlet, the gas inlet being configured to receive a flow of as into the humidification chamber and the gas outlet configured to release the flow of gas from the humidification chamber;
a heating element configured to controllably heat liquid within the humidification chamber separately from the liquid held in the holding chamber such that the flow of gas through the humidification chamber from the gas inlet to the gas outlet is humidified b the heated liquid;
a partition configured to divide the humidification chamber from the holding chamber, wherein the partition defines an opening between the humidification chamber and the holding chamber such that fluid is communicated between the humidification chamber and the holding chamber through the opening, and wherein the opening is formed such that the partition and liquid held in the humidification chamber isolate the flow path formed by humidification chamber from the holding chamber causing the flow of gas through the humidification chamber to result in pressurization of the humidification chamber that reduces the level of liquid within the humidification chamber to a level that is substantially lower than the level of liquid in the holding chamber;
a unitary base structure configured to form a base surface of the humidification chamber and the holding chamber, and at least one side wall of the humidification chamber; and
a unitary partition structure configured to form the partition and a ceiling of the humidification chamber, wherein the unitary base structure forms the gas inlet and the unitary partition structure forms the gas outlet.

12. The humidifier of claim 11, wherein the holding chamber at least partially surrounds the humidification chamber.

13. The humidifier of claim 11, wherein the humidification chamber is sealed from ambient atmosphere, and wherein the holding chamber forms a secondary opening that places the holding chamber in restrictive communication with ambient atmosphere.

14. The humidifier of claim 11, wherein the opening formed by the partition is configured such that liquid from the holding chamber replenishes the liquid within the humidification chamber as the liquid within the humidification chamber is vaporized and carried out of the humidifier by the flow of gas.

* * * * *